United States Patent [19]
Tokumoto et al.

[11] Patent Number: 5,166,419
[45] Date of Patent: Nov. 24, 1992

[54] METHOD FOR PREPARING ALPHA-(4-ISOBUTYLPHENYL) PROPIONIC ACID OR ITS PRECURSOR

[75] Inventors: Yuuichi Tokumoto; Isoo Shimizu, both of Yokohama; Satoru Inoue, Kawasaki, all of Japan

[73] Assignee: Nippon Petrochemicals Co., Ltd., Tokyo, Japan

[21] Appl. No.: 571,178

[22] Filed: Aug. 22, 1990

[30] Foreign Application Priority Data

Aug. 25, 1989 [JP] Japan .................... 1-220009

[51] Int. Cl.$^5$ ............................. C07C 51/10
[52] U.S. Cl. .................... 562/406; 560/105; 568/428; 568/429
[58] Field of Search ............ 562/406; 560/105; 568/428, 429

[56] References Cited

U.S. PATENT DOCUMENTS

| | | | |
|---|---|---|---|
| 4,350,825 | 9/1982 | Huang | 562/406 |
| 4,620,027 | 10/1986 | Hsu | 562/406 |
| 4,694,100 | 9/1987 | Shimizu et al. | 560/105 |
| 4,739,110 | 4/1988 | Drent | 560/207 |
| 4,827,065 | 7/1989 | Shimizu et al. | 585/25 |
| 4,855,518 | 8/1989 | Shimizu et al. | 585/319 |
| 4,855,519 | 8/1989 | Shimizu et al. | 585/319 |
| 4,981,995 | 1/1991 | Elango et al. | 562/406 |

FOREIGN PATENT DOCUMENTS 170147 5/1980 European Pat. Off. .
2006431 10/1990 Japan .

*Primary Examiner*—Paul J. Killos
*Attorney, Agent, or Firm*—Scully, Scott, Murphy & Presser

[57] ABSTRACT

A method for preparing α-(4-isobutylphenyl)propionic acid or its precursor is here disclosed which comprises the following steps (I), (II) and (III):

step (I): subjecting isobutylbenzene and a polyalkylbenzene to disproportionation reaction in order to form p-isobutylethylbenzene step (II): dehydrogenating p-isobutylethylbenzene obtained in the step (I) to form p-isobutylstyrene, and step (III): the following step (IIIa) or (IIIb):

step (IIIa): reacting p-isobutylstyrene obtained in the step (II) with carbon monoxide and hydrogen to prepare α-(4-isobutylphenyl)propionaldehyde, or step (IIIb): reacting p-isobutylstyrene obtained in the preceding step (II) with carbon monoxide and water or a lower alcohol to prepare α-(4-isobutylphenyl)propionic acid or its alkyl ester.

13 Claims, 1 Drawing Sheet

METHOD FOR PREPARING ALPHA-(4-ISOBUTYLPHENYL) PROPIONIC ACID OR ITS PRECURSOR

BACKGROUND OF THE INVENTION (i) Field of the Invention

The present invention relates to a method for preparing α-(4-isobutylphenyl)propionic acid or its precursor, i.e., an alkyl α-(4-isobutylphenyl)propionate or α-(4-isobutylphenyl)propionaldehyde at a low cost and in a high purity.

α-(4-Isobutylphenyl)propiopic acid is a useful medicine (trade name Ibuprophen) having pharmacological effects such as alleviation effects of fever and pain and antiphlogistic effect, as described in British Patent No. 971700 and French Patent No. 1549758.

On the other hand, it is known that the alkyl α-(4-isobutylphenyl)propionate can be easily converted into α-(4-isobutylphenyl)propionic acid by hydrolysis with an acid or an alkali in a known manner. Furthermore, it is also known that α-(4-isobutylphenyl)propionaldehyde can be easily converted into α-(4-isobutylphenyl)propionic acid by oxidization in a known manner. Therefore, each of these compounds can be considered to be the precursor of α-(4-isobutylphenyl)propionic acid.

(ii) Description of the Prior Art

Heretofore, α-(4-isobutylphenyl)propionic acid or its precursor has been synthesized from an extremely great number of compounds as starting materials by various methods. However, in order to synthesize α-(4-isobutylphenyl)propionic acid or its precursor at a low cost and in a high purity, the following requirements are needful:

(a) Starting materials should be simple compounds.

(b) In a reaction to be utilized, an intermediate in the each step should also be as simple and stable as possible.

(c) In place of expensive reagents, inexpensive reagents or catalysts should be employed.

(d) The number of steps for the synthesis should be as few as possible.

(e) Since an isobutyl group is liable to bring about isomerization, it is necessary to use a reaction in which the isomerization and other undesirable phenomenons are inhibited to the utmost.

For example, in U.S. Pat. No. 3959364 which suggests synthetic methods of α-(4-isobutylphenyl)propionic acid or its alkyl ester, expensive starting materials are used, or reagents such as Grignard reagents which are unstable and difficult to handle are used. Therefore, these methods are not considered to be inexpensive and economical.

In methods described in French Patent No. 1549758, British Patent Nos. 1160725 and 1549140 and U.S. Pat. Nos. 3965161 and 4143229, p-isobutylacetophenone is used as the starting material.

However, in the manufacture of p-isobutylacetophenone, expensive and unstable material and reagent are used, and it is additionally necessary to treat a large amount of acidic wastes so as to make them harmless. Furthermore, the conversion of p-isobutylacetophenone into α-(4-isobutylphenyl)propionic acid proceeds via intricate intermediates, and it is not always fair to say that these known methods are economical from an industrial viewpoint.

U.S. Pat. No. 4329507 suggests a method for preparing α-(4-isobutylphenyl)propionic acid from p-isobutylstyrene through a carbonylation reaction. This method is industrially useful, because p-isobutylstyrene which is the starting material is simple and stable, and because the carbonylation reaction does not require expensive reagents. However, in a conventional manufacturing method of p-isobutylstyrene, a complex reaction route is taken or expensive reagents are employed, so that the above-mentioned advantages are lost.

U.S. Pat. No. 4694100 discloses a method which comprises subjecting isobutylbenzene and acetaldehyde to condensation reaction in the presence of a sulfuric acid catalyst to form 1,1-bis(p-isobutylphenyl)ethane, and then catalytically decomposing the latter by the use of an acid catalyst to prepare p-isobutylstyrene. However, since the above-mentioned method employs sulfuric acid, the sulfonation reaction of isobutylbenzene itself which is the valuable raw material cannot be avoided in the step of forming 1,1-bis(p-isobutylphenyl)ethane, which leads to a heavy loss. In addition, since this condensation reaction is a dehydration reaction, the used sulfuric acid is diluted with the resulting water, so that its concentration is low. Additionally, a great deal of the sulfonated compound is dissolved in the sulfonic acid phase, and therefore the resulting water must be removed through chemical reaction by the use of anhydrous sulfuric acid or fuming sulfuric acid, with the result that the cost of the catalyst also increases.

In consequence, it is desired to develop a method for preparing p-isobutylstyrene at a low cost.

The present inventors have conceived the dehydrogenation of p-isobutylethylbenzene as a direct method for manufacturing p-isobutylstyrene inexpensively. However, the prior art regarding the dehydrogenation of p-isobutylethylbenzene is not present at all, and any similar techniques are not known, either. In other words, there are not known techniques so far which selectively dehydrogenate one specific substituent of a polyalkylbenzene such as p-isobutylethylbenzene having a plurality of alkyl groups which are different in structure and which may be all dehydrogenated.

For example, European Patent No. 93518 discloses a method for preparing methylstyrene by dehydrogenating methylethylbenzene; British Patent No. 2068253 discloses a method for preparing tert-butylstyrene by dehydrogenating tert-butylethylbenzene; and European Patent No. 217492 discloses a method for preparing ethylstyrene or divinylbenzene by dehydrogenating diethylbenzene. However, each of methylethylbenzene and tert-butylethylbenzene has an ethyl group which may be dehydrogenated and other substituents of a methyl group and a tert-butyl group which cannot be dehydrogenated. Therefore, the selectivity of the dehydrogenation reaction itself is not considered. Furthermore, with regard to diethylbenzene having two ethyl groups which may be dehydrogenated, it is unnecessary to consider the selectivity, because the two ethyl groups are not different.

However, the technique of the present invention for preparing p-isobutylstyrene by the selective dehydrogenation of p-isobutylethylbenzene is basically different from these known techniques. In the concrete, the substituents bonded to the aromatic ring of p-isobutylethylbenzene which is the raw material are an ethyl group and an isobutyl group, and these groups can be converted into a vinyl group and a 2-methyl-1-propenyl group or a 2-methyl-2-propenyl group (hereinafter referred to as "substituted propenyl group" sometimes) by the dehydrogenation. That is, when the ethyl group alone of p-isobutylethylbenzene is dehydrogenated, p-isobutylstyrene is formed, and when the isobutyl group alone is dehydrogenated, 4-(2'-methyl-1'-propenyl)ethylbenzene or 4-(2'-methyl-2'-propenyl)ethylbenzene is formed. Furthermore, when both of the ethyl group and the isobutyl group are dehydrogenated, 4-(2'-methyl-1'-propenyl)vinylbenzene or 4-(2'-methyl-2'-propenyl)vinylbenzene is formed. As is apparent from the foregoing, p-isobutylethylbenzene has the two different alkyl groups which can be dehydrogenated, and the product utterly depends upon the group to be dehydrogenated.

As understood from known literature such as Journal of Catalysis 34, p. 167–174 (1974) and Azerb. Khim. Zh., (2), p. 59–62 (Russ) (1968), a branched isopropyl group is dehydrogenated about twice to thrice more easily than a straight-chain ethyl group. According to the investigation of the present inventors, it has been confirmed that when p-sec-butylbenzene is dehydrogenated in the presence of an iron oxide catalyst, the sec-butyl group is about twice more easily dehydrogenated than the ethyl group. From this fact, it can be presumed that the branched sec-butyl group having 4 carbon atoms is more easily dehydrogenated than the straight-chain ethyl group, as described in the above-mentioned literature regarding isopropylethylbenzene. However, such a conception cannot achieve the object of the present invention.

That is, the product which is intended by the dehydrogenation step of p-isobutylethylbenzene is p-isobutylstyrene in which the ethyl group alone is dehydrogenated. Therefore, it is strongly demanded to develop a dehydrogenation method of p-isobutylethylbenzene in which the selectivity of p-isobutylstyrene is high, i.e., a method for selectively dehydrogenating the ethyl group alone of the ethyl and isobutyl groups.

Furthermore, another manufacturing method of p-isobutylethylbenzene is known which comprises reducing 1-(4-ethylphenyl)-2-methylpropane-1-one with potassium hydroxide and hydrazine in a solvent of diethylene glycol, as described in, for example, Beilstein, EIV5 (Sys. Nr. 470/H445). However, in this method, 1-(4-ethylphenyl)-2-methylpropane-1-one which is the raw material is very expensive, and hydrazine which is very dangerous to handle must be used as a reducing agent, which disturbs the industrialization of this method unpreferably. Moreover, it is known that p-isobutylethylbenzene is obtained as a by-product in the catalytic cracking reaction of 1,1-bis(p-isobutylphenyl)ethane, as disclosed in examples of U.S. Pat. No. 4827065. However, in this method, p-isobutylethylbenzene is the by-product, and therefore the production is unpreferably too low. As understood from the foregoing, the manufacturing examples of p-isobutylethylbenzene by the conventional techniques are very limited and are uneconomical. Therefore, it is strongly demanded to develop a method for manufacturing p-isobutylethylbenzene inexpensively.

SUMMARY OF THE INVENTION

The present invention is directed to a method for preparing α-(4-isobutylphenyl)propionic acid or its precursor industrially and economically which comprises the following steps (I), (II) and (III):

step (I): subjecting isobutylbenzene and a polyalkylbenzene represented by the following formula (I) to disproportionation reaction at a reaction temperature of from −10° to 600° C. in the presence of an acid catalyst in order to form p-isobutylethylbenzene

$R_1$ is $(-CH_3)_m$ or $(-C_2H_5)_m$, $R_2$ is $(-C_2H_5)_n$, and each of m and n is an integer of from 1 to 5 which meets $2 \leqq m+n \leqq 6$, step (II): dehydrogenating p-isobutylethylbenzene obtained in the above-mentioned step (I) at a reaction temperature of from 300 to 650° C under a reaction pressure of 50 kg/cm² or less for a contact time of 0.005 to 20 seconds at a p-isobutylethylbenzene conversion of 80% by weight or less in a gaseous phase in the presence of a dehydrogenation metal catalyst containing a metal selected from the group consisting of metals in the groups Ib, IIb, VIa, VIIa and VIII of the periodic table in order to form p-isobutylstyrene, and step (III): the following step (IIIa) or (IIIb):

step (IIIa): reacting p-isobutylstyrene obtained in the preceding step (II) with carbon monoxide and hydrogen at a reaction temperature of from 40° to 150° C. under a mixed pressure of from 10 to 600 kg/cm² in the presence of a transition metal complex carbonylation catalyst in order to prepare α-(4-isobutylphenyl)propionaldehyde, or step (IIIb): reacting p-isobutylstyrene obtained in the preceding step (II) with carbon monoxide and water or a lower alcohol at a reaction temperature of from 40° to 250° C. under a carbon monoxide pressure of from 10 to 600 kg/cm² in the presence of a transition metal complex carbonylation catalyst in order to prepare α-(4-isobutylphenyl)propionic acid or its alkyl ester.

DETAILED DESCRIPTION OF THE INVENTION

Figure 1:
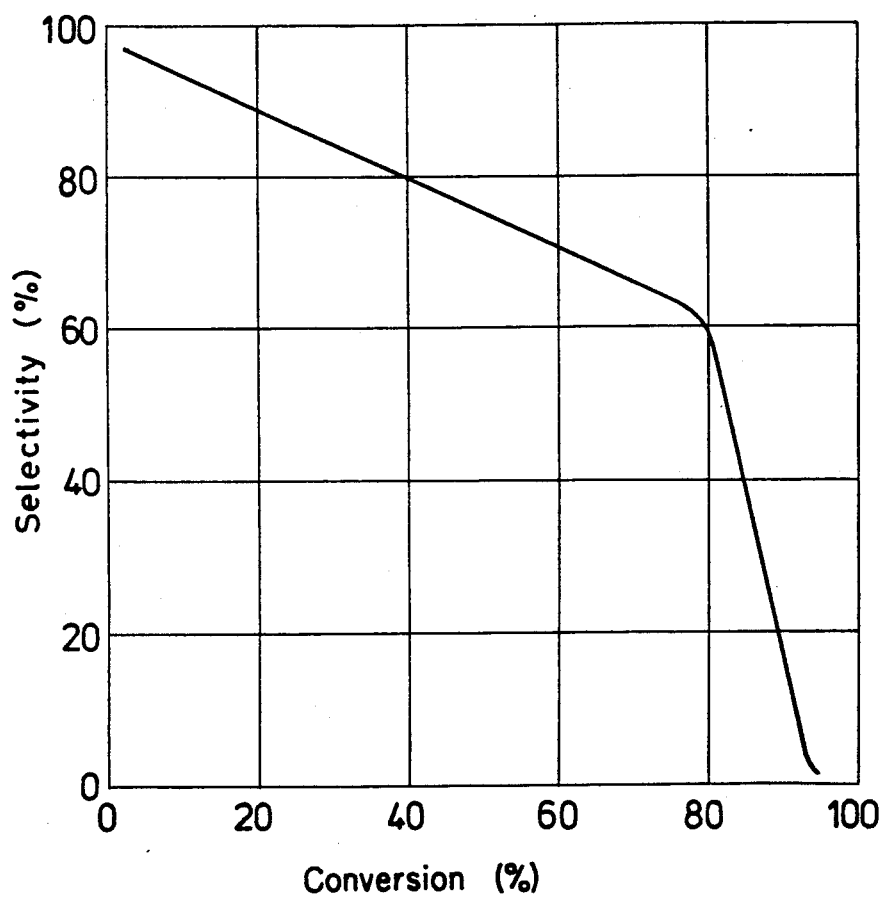
FIG. 1 shows a relation between the conversion of PBE and the selectivity of PBS in a dehydrogenation reaction, and in this drawing, the solid line represents the results of Experimental Examples 33 to 42 of the present invention.

Now, the present invention will be described in more detail.

The step (I) of the present invention is the step where isobutylbenzene and a polyalkylbenzene represented by the following formula (I) are subjected to the disproportionation reaction in the presence of the acid catalyst in order to form p-isobutylethylbenzene.

In the step (I), the polyalkylbenzene is required to have at least one ethyl group on the benzene nucleus. However, ethylbenzene which is a monoalkylbenzene is unpreferable, because the disproportionation activity of the ethyl group is too low to achieve the objects of the present invention.

That is, in order to exert the sufficient activity in the disproportionation reaction of the present invention, the polyalkylbenzene must possess at least one ethyl group on the benzene nucleus and at least two alkyl groups in all. It has been found by the investigation of the present inventors that the more the number of the alkyl substituents is, the higher the disproportionation activity is.

Furthermore, it has also been found that if the above-mentioned polyalkyl benzene has at least one ethyl group as the alkyl group, the other alkyl group need not be the ethyl group. Generally, in the disproportionation reaction of the alkylbenzene, the higher the grade of the carbon at its benzyl position is, the higher the activity of the alkyl group to be replaced is, and in the present invention, it is preferred that an alkyl group other than the ethyl group is not moved. Therefore, the alkyl group other than the ethyl group (the carbon at the benzyl position is secondary) is required to be the methyl group (the carbon at the benzyl position is primary). That is the reason why the polyalkylbenzene having the plural ethyl groups or having the ethyl group and the methyl group represented by the above formula is employed in the present invention.

Typical examples of the polyalkylbenzene represented by the aforesaid formula include diethylbenzene, triethylbenzene, tetraethylbenzene, pentaethylbenzene, hexaethylbenzene, ethyltoluene, diethyltoluene, triethyltoluene, tetraethyltoluene, pentaethyltoluene, ethylxylene, diethylxylene, triethylxylene, tetraethylxylene, trimethylethylbenzene, trimethyldiethylbenzene, trimethyltriethylbenzene, tetramethylethylbenzene, tetramethyldiethylbenzene and pentamethylethylbenzene.

In the disproportionation reaction, a usual acid catalyst can be used, if conditions where the isomerization of the isobutyl group is inhibited are employed. Examples of the acid catalyst for the disproportionation reaction include solid acids such as silica-alumina and zeolite; inorganic acids such as sulfonic acid, phosphoric acid and hydrogen fluoride; organic acids such as benzenesulfonic acid, p-toluenesulfonic acid and trifluoromethanesulfonic acid; Friedel-Crafts catalysts such as aluminum chloride, zirconium chloride, zinc chloride, vanadium chloride, titanium chloride, beryllium chloride and boron fluoride; heteropoly-acids such as silicotungstic acid and phosphomolybdic acid; isopoly-acids; and strong acid type ion exchange resins typified by a perfluorosulfonic acid resin such as the trade name "Nafion" resin.

The reaction temperature can be suitably selected, depending upon the catalyst. Usually, it is selected from the range of from −10° to 600° C., but in this case, much attention should be paid so as to inhibit cracking reaction and the isomerization of the isobutyl group to the utmost. When the reaction temperature is less than the above-mentioned range, a reaction rate is unpreferably too late. Conversely, when it is higher than the range, the cracking reaction or the structural isomerization of the isobutyl group occurs noticeably.

Next, some preferable disproportionation catalysts will be described in detail.

In case silica-alumina is used as the disproportionation catalyst, the silica-alumina may be a natural or a synthetic type, or a mixture thereof. The reaction temperature is preferably from 150° to 600° C., more preferably from 200° to 500° C.

In case zeolite is used as the disproportionation catalyst, examples of the usable zeolite include an HX type zeolite, an HY type zeolite and a material containing hydrogen zeolite such as hydrogen faujasite. This kind of hydrogen zeolite shows a strong solid acidity and can be made by subjecting, to cation exchange, an alkali metal salt of a zeolite such as an NaX zeolite, an NaY zeolite or an Na faujasite so as to convert a part or all of the alkali metal into a proton type. In this case, the reaction temperature is preferably from 100° to 400° C., more preferably from 110° to 350° C.

In case trifluoromethanesulfonic acid and/or hydrogen fluoride is used as the catalyst, trifluoromethanesulfonic acid or hydrogen fluoride may be used in the form of a pure product, an aqueous solution or a mixture thereof. As a result of the researches of the present inventors, it has been found that trifluoromethanesulfonic acid and hydrogen fluoride have about the same catalytic effect in the disproportionation of isobutylbenzene, and they provide about the same products under the same conditions. In this case, the reaction temperature is preferably from −10° to 200° C., more preferably In case aluminum chloride is used as the catalyst, the reaction temperature is in the range of from 0° to 150° C., preferably from 5° to 100° C.

In case the heteropoly acid is used as the catalyst, examples of the usable heteropoly acid include various heteropoly acids of molybdenum and tungsten, and usable examples of the hetero-atom include P, B, V, As, Si, Ge, Sn, Ti, Zr, Ce, Th, Fe, Pt, Mn, Co, Ni, Te, I, Al, Cr, Rh, Cu and Se. In this case, the reaction temperature is preferably from 150° to 600° C., more preferably from 200° to 500° C.

When a strong acid type cation exchange resin such as Naphion resin is used, the suitable reaction temperature is from 50° to 300° C., preferably 100° to 250° C.

No particular restriction is put on the solvent, so long as it does not have a bad influence on the disproportionation reaction and the undermentioned separation/purification of p-isobutylethylbenzene. However, sufficiently preferable results can be obtained usually in the state of non-solvent. No particular restriction is put on the reaction pressure.

The disproportionation reaction can be achieved by either of a batch system and a flow system.

In every reaction product obtained under the above-mentioned conditions, isobutylethylbenzene is present in the form of a mixture of o-isobutylethylbenzene, m-isobutylethylbenzene and p-isobutylethylbenzene. According to the researches of the present inventors, it has been found that the separation of p-isobutylethylbenzene from the position isomer mixture can be accomplished by distillation under specific conditions.

That is, a feed flow to be fed into a distillation column should be the isobutylethylbenzene position isomer mixture in which the weight ratio of p-isobutylethylbenzene to the weight of the mixture is 5% or more, preferably 10% or more. When the ratio of the weight of the p-isomer to the total weight of the isobutylethylbenzene position isomer mixture is less than 5%, the content of the desired component in the mixture is too low, so that high-purity p-isobutylethylbenzene cannot be effectively separated even by the use of rectification. Components other than isobutylethylbenzene may be contained in the mixture, and no particular restriction is put on these components, so long as they do not hinder the achievement of the object of the distillation step of the present invention.

Furthermore, in the distillation column used in the distillation step, the number of theoretical plates is 20 or more, preferably 30 or more. When the number of the theoretical plates is less than 20, high-purity p-isobutylethylbenzene cannot be separated effectively by the distillation. No particular restriction is put on the upper limit of the theoretical plate number, but when the number is too many, the distillation operation is only uneconomical. Therefore, a theoretical plate number of up to 500 is enough.

In the above-mentioned distillation, p-isobutylethylbenzene is recovered as a fraction mainly comprising components in a boiling point range of 213° to 216° C. in terms of atmospheric pressure. The fraction other than this p-isobutylethylbenzene fraction contains benzene derivatives having an isobutyl group, an ethyl group and a methyl group, and needless to say, a part or all of the other fraction can be reused as the raw material of the aforesaid step (I).

A distillation process is not particularly limited, and a continuous system or a batch system, reduced pressure, atmospheric pressure or applied pressure, and a single-column system or a multi-column system can be optionally chosen.

The step (II) in the method of the present invention is the step where p-isobutylethylbenzene obtained in the step (I) is dehydrogenated in a gaseous phase with a dehydrogenation metal catalyst in order to form p-isobutylstyrene. Concretely, the only ethyl group of p-isobutylethylbenzene is selectively dehydrogenated at a reaction temperature of 300° to 650° C. under a reaction pressure of 50 kg/cm$^2$ or less for a contact time of 0.05 to 20 seconds at a p-isobutylethylbenzene conversion of 80% by weight or less in the presence of a dehydrogenation metal catalyst containing a metal selected from the group consisting of metals in the groups Ib, IIb, VIa, VIIa and VIII of the periodic table in order to form p-isobutylstyrene.

Typical examples of the dehydrogenation catalyst include metallic compounds of iron, copper, zinc, nickel, palladium, platinum, cobalt, rhodium, iridium, ruthenium, chromium and molybdenum, and combinations of these compounds may be also used effectively. These metals can be used in the form of a simple substance or in the form of an oxide, a sulfide or a hydrogen-treated compound. The preferable catalyst contains at least one metal selected from iron, copper and chromium. In particular, the iron oxide catalyst and the copper-chromium catalyst are effective for the objects of the present invention, since they have the high selectivity of p-isobutylstyrene.

The reaction temperature of the dehydrogenation depends upon the composition of the catalyst, the contact time and a molar ratio at the time of dilution, but it is selected in the range of from 300° to 650° C., preferably 400° to 650° C. When the reaction temperature is higher than this range, a secondary reaction such as the further dehydrogenation of the produced p-isobutylstyrene occur vigorously, so that the selectivity coefficient of p-isobutylstyrene deteriorates noticeably. In consequence, a great deal of p-isobutylethylbenzene is lost, and the distribution of the products is complicated fairly, with the result that it is difficult to separate p-isobutylstyrene and p-isobutylethylbenzene by the distillation or the like. When the reaction temperature is lower than the above-mentioned range, a reaction rate lowers perceptibly, which is not economical, though the selectivity of p-isobutylstyrene is high.

The olefin formed by the dehydrogenation reaction is polymerizable, and thus if it is kept up at a high temperature in a high concentration in a reactor, a part of the produced p-isobutylstyrene is polymerized and lost. In order to effectively avoid this undesirable phenomenon, it is effective that the concentration of the olefin is diluted by feeding the material together with a non-reducing gas such as a nitrogen gas, a helium gas, an argon gas, steam or an oxygen gas. Alternatively, the dilution may be made with a solvent such as benzene which is hardly dehydrogenated. Furthermore, in order to maintain the catalyst activity for the dehydrogenation, steam can be fed to the reactor in the course of the dehydrogenation. The amount of steam is not particularly limited.

The object of the dehydrogenation step (II) of the present invention may be achieved by any reaction system of a fixed bed, a moving bed and a fluidized bed.

The reaction pressure for the dehydrogenation is not particularly limited, so long as it permits vaporizing p-isobutylstyrene produced under the above-mentioned reaction conditions. Nevertheless, the reaction pressure is usually from atmospheric pressure to 50 kg/cm$^2$ or less from an economical viewpoint.

The time of contact with the raw material p-isobutylethylbenzene is in the range of 0.005 to 20 seconds, preferably 0.01 to 10 seconds, more preferably 0.05 to 5 seconds. When the contact time is less than the above-mentioned range, reaction efficiency is inconveniently low. When it is more than the above-mentioned range, produced p-isobutylstyrene is further secondarily dehydrogenated, and the selectivity of p-isobutylstyrene lowers unpreferably. The contact time can be suitably altered in the abovementioned range in accordance with the combination of the selected reaction system, the composition of the reaction gas, the composition of the catalyst, the reaction temperature, the preheating temperature of the raw material gas and the like.

Needless to say, the dehydrogenation step (II) can be carried out by a continuous system or a batch system. Anyway, in the present invention, it is important that p-isobutylethylbenzene is converted into p-isobutylstyrene efficiently by the dehydrogenation.

In the foregoing, the influence of the reaction conditions and factors on the reaction in the dehydrogenation step (II) of the present invention has been discussed, and in this connection, the researches of the present inventors have elucidated that when the dehydrogenation of p-isobutylethylbenzene is carried out under the conditions of the present invention, the influence of the reaction conditions and factors on the reaction can be represented by a relation between the conversion of p-isobutylethylbenzene and the selectivity of p-isobutylstyrene. That is, the selectivity of p-isobutylstyrene with respect to the conversion of p-isobutylethylbenzene obtained under the above-mentioned reaction conditions is in a linear relation (hereinafter referred to as "dehydrogenation performance straight line"). FIG. 1 shows an exemplary dehydrogenation performance straight line obtained from the undermentioned examples. For example, if certain factors of the reaction conditions are set, a point on the dehydrogenation performance straight line corresponding to a certain conversion indicates the selectivity of p-isobutylstyrene which will be actually obtained. Therefore, the reaction conditions can be chosen so as to obtain the conversion of p-isobutylethylbenzene corresponding to the desired selectivity in accordance with the dehydrogenation performance straight line of the used dehydrogenation catalyst. For example, in the case of the copper-chromium catalyst, it is suitable in the present invention that the conversion of p-isobutylethylbenzene is maintained at 80% by weight or less, preferably 60% by weight or less, more preferably 50% by weight. Furthermore, in the case of the iron oxide catalyst, it is suitable in the present invention that the conversion of p-isobutylethylbenzene is maintained preferably at 80% by weight or less, more preferably 70% by weight or less. If the conversion is in excess of the range, the selectivity of p-isobutylstyrene deteriorates rapidly and diverges from the dehydrogenation performance straight line, so that cracked products increase unpreferably. In case the conversion is in the above-mentioned range, the lower the conversion is, the higher the selectivity is. However, the productivity of p-isobutylstyrene is the product of the conversion and the selectivity, and therefore the employment of the low conversion is unpreferable, because the separation and recovery operation of unreacted p-isobutylethylbenzene by the subsequent distillation is very burdensome. From an economical viewpoint, it is desirable that the conversion is maintained at a level of 5% by weight or more.

In the step (III) of the present invention, p-isobutylstyrene obtained in the preceding step (II) is carbonylated to prepare α-(4-isobutylphenyl)propionic acid or its precursor.

In this carbonylation, there are the step (IIIa) of reacting p-isobutylstyrene with carbon monoxide and hydrogen and the step (IIIb) of the hydrocarboxylation in which p-isobutylstyrene is reacted with carbon monoxide and water or the hydroesterification in which p-isobutylstyrene is reacted with carbon monoxide and a lower alcohol.

In the first place, reference will be made to the hydroformylation (IIIa) in which p-isobutylstyrene is reacted with carbon monoxide and hydrogen.

In the step (IIIa) of the present invention, p-isobutylstyrene obtained in the preceding step (II) is subjected to the hydroformylation with carbon monoxide and hydrogen in the presence of a transition metal complex catalyst in order to be converted into α-(4-isobutylphenyl)propionaldehyde.

The transition metal complex catalyst used in the above-mentioned hydroformylation is a complex catalyst comprising a transition metal of palladium, rhodium, iridium or ruthenium. These usable transition metals have oxidation numbers of from 0 to a maximum oxidation number, and each of these transition metals is used in combination with a halogen atom, a trivalent phosphorus compound, a π-allyl group, an amine, a nitrile, an oxime, an olefin or a carbonyl complex compound having carbon monoxide and hydrogen as ligands.

Typical examples of the transition metal complex catalyst include bistriphenylphosphinedichloro complex, bistributylphosphinedichloro complex, bistricyclohexylphosphinedichloro complex, π-allyltriphenylphosphinedichloro complex, triphenylphosphinepiperidinedichloro complex, bisbenzonitriledichloro complex, biscyclohexyloximedichloro complex, 1,5,9-cyclododecatriene-dichloro complex, bistriphenylphosphinedicarbonyl complex, bistriphenylphosphine acetate complex, bistriphenylphosphine dinitrate complex, bistriphenylphosphine sulfate complex and tetrakistriphenylphosphine complex, and chlorocarbonylbistriphenylphosphine complex, hydridocarbonyltristriphenylphosphine complex, bischlorotetracarbonyl complex and dicarbonylacetyl acetonate complex having carbon monoxide as a part of the ligands.

The catalyst can be fed in the form of the complex to the reaction system, or alternatively the compound which will be the ligand is fed separately to the reaction system, and the complex can be then formed and used in the reaction system. That is, in this case, an oxide, a sulfate or a chloride of the above-mentioned transition metal is fed to the reaction system simultaneously together with a compound which will be the ligand, for example, a phosphine, a nitrile, an allyl compound, an amine, an oxime or an olefin, or carbon monoxide or hydrogen.

Examples of the phosphine include triphenylphosphine, tritolylphosphine, tributylphophine, tricyclohexylphosphine and triethylphosphine; examples of the nitrile include benzonitrile, acrylonitrile, propionitrile and benzylnitrile; examples of the allyl compound include allylchloride and allylalcohol; examples of the amine include benzylamine, pyridine, piperazine and tri-n-butylamine; examples of the oxime include cyclohexyloxime, acetoxime and benzaldoxime; and examples of the olefin include 1,5-cyclooctadiene and 1,5,9-cyclododecatriene.

The amount of the complex catalyst or the compound capable of forming the complex is from 0.0001 to 0.5 mole, preferably 0.001 to 0.1 mole, with respect to 1 mole of p-isobutylstyrene. Furthermore, the amount of the compound which will be the ligand is from 0.8 to 10 moles, preferably 1 to 4 moles with respect to 1 mole of the transition metal, which will be the nucleus of the complex, such as palladium, rhodium, iridium or ruthenium.

For the purpose of accelerating the reaction, an inorganic halide such as hydrogen chloride or boron trifluoride, or an organic iodide such as methyl iodide may be added to the reaction system, When this kind of halide is added, the amount of the halide is from 0.1 to 30-fold moles, preferably 1 to 5-fold moles in terms of a halogen atom with regard to 1 mole of the complex catalyst or the compound capable forming the complex. When the amount of the halide is less than 0.1-fold mole, the effect of the added halide is not perceptible sometimes, depending upon the kind of catalyst. When it is in excess of 30-fold moles, the activity of the catalyst deteriorates reversely, and the halogen atom is added to a double bond of p-isobutylstyrene, so that the intended reaction is inhibited unpreferably.

The hydroformylation reaction is carried out at a temperature of from 40° to 150° C., preferably from 55° to 110° C. When the reaction temperature is less than 40° C., a reaction rate is too low to actually achieve the hydroformylation. When it is more than 150° C., secondary reactions such as polymerization and the addition of hydrogen as well as the decomposition of the complex catalyst tend to occur unpreferably.

The reaction pressure for the hydroformylation is in the range of from 10 to 600 kg/cm$^2$ in terms of a mixed pressure of carbon monoxide and hydrogen. When the reaction pressure is less than 10 kg/cm$^2$, a reaction rate is too low to actually achieve the hydroformylation. The higher the pressure is, the faster the reaction proceeds, but when the pressure is too high, it is required to sufficiently heighten the pressure resistance of a reactor. Therefore, it is natural that the upper limit of the reaction pressure is present, and it is 600 kg/cm$^2$ in practice.

The reaction is allowed to proceed until a mixed gas of carbon monoxide and hydrogen is not absorbed any more, and a reaction time is usually in the range of from 4 to 20 hours.

Carbon monoxide and hydrogen necessary for the reaction may be fed to the reactor in the state of a mixed gas or separately. A molar ratio between carbon monoxide and hydrogen to be fed to the reactor can be suitably selected. That is, in the hydroformylation reaction of the present invention, carbon monoxide and hydrogen are absorbed and consumed accurately in a molar ratio of 1:1. In consequence, it is most effective to feed carbon monoxide and hydrogen in a molar ratio of 1:1, depending upon the size of the reactor and the system of the reaction.

In the hydroformylation of the present invention, a solvent which is inactive to the hydroformylation can be used for the purpose of removing reaction heat and the like. Examples of the solvent which is inactive to the hydroformylation include polar solvents such as an ether and a ketone, and non-polar solvents such as a paraffin, a cycloparaffin and an aromatic hydrocarbon. However, even if no solvent is used, sufficiently preferable results can be usually obtained.

After completion of the hydroformylation reaction, the reaction product is easily separated into the aimed high-purity compound α-(4-isobutylphenyl)propionaldehyde and the catalyst preferably under reduced pressure by the distillation. The recovered complex catalyst can be reused.

α-(4-Isobutylphenyl)propionaldehyde obtained by the present invention can be oxidized in a usual manner in order to be easily converted into α-(4-isobutylphenyl)propionic acid. The oxidation can be performed by a known manner of oxidizing an aldehyde to a carboxylic acid, for example, chrominum oxidation, hypochlorous acid oxidation or permanganic acid oxidation.

Next, reference will be made to the hydrocarboxylation regarding the reaction with carbon monoxide and water, and to the hydroesterification step (IIIb) regarding the reaction with carbon monoxide and a lower alcohol.

In the hydrocarboxylation reaction, p-isobutylstyrene is reacted with carbon monoxide and water to form α-(4-isobutylphenyl)propionic acid. Furthermore, in the hydroesterification reaction, p-isobutylstyrene is reacted with carbon monoxide and the lower alcohol to form an alkyl ester of α-(4-isobutylphenyl)propionic acid. For example, if methyl alcohol is caused to take part in the reaction, methyl α-(4-isobutylphenyl)propionate is obtained.

Examples of the transition metal complex catalyst used in the aforesaid step (IIIb) include complexes of transition metals such as palladium, rhodium and iridium, and the particularly preferable catalyst is the complex of palladium. The transition metal can be used in combination with a halogen atom, a trivalent phosphorus compound or a carbonyl complex compound and carbon monoxide as a ligand. One example of the usable transition metal is palladium having a valence of 0 to 2.

Typical examples of the transition metal complex catalyst include bistriphenylphosphinedichloro complex, bistributylphosphinedichloro complex, bistricyclohexylphosphinedichloro complex, π-allyltriphenylphosphinedichloro complex, triphenylphosphinepiperidinedichloro complex, bisbenzonitriledichloro complex, biscyclohexyloximedichloro complex, 1,5,9-cyclododecatriene-dichloro complex, bistriphenylphosphinedicarbonyl complex, bistriphenylphosphine acetate complex, bistriphenylphosphine dinitrate complex, bistriphenylphosphine sulfate complex and tetrakistriphenylphosphine complex, and chlorocarbonylbistriphenylphosphine complex, hydridocarbonyltristriphenylphosphine complex, bischlorotetracarbonyl complex and dicarbonylacetyl acetonate complex having carbon monoxide as a part of the ligands.

The catalyst can be fed in the form of the complex to the reaction system, or alternatively the compound which will be the ligand is fed separately to the reaction system, and the complex will be formed and used in the reaction system.

The amount of the complex catalyst or the compound capable of forming the complex is from 0.0001 to 0.5 mole, preferably 0.001 to 0.1 mole, with respect to 1 mole of p-isobutylstyrene. Furthermore, the amount of the compound which will be the ligand is from 0.8 to 10 moles, preferably 1 to 4 moles with respect to 1 mole of the transition metal, which will be the nucleus of the complex, such as palladium, rhodium or iridium.

For the purpose of accelerating the reaction, an inorganic halide such as hydrogen chloride or boron trifluoride may be added to the reaction system.

The amount of the halide is from 0.1 to 30-fold moles, preferably 1 to 15-fold moles in terms of a halogen atom with regard to 1 mole of the complex catalyst or the compound capable of forming the complex. When the amount of the halide is less than 0.1-fold mole, the effect of the added halide is not perceptible sometimes, depending upon the kind of catalyst. When it is in excess of 30-fold moles, the activity of the catalyst deteriorates reversely, and a halogen atom is added to a double bond of p-isobutylstyrene, so that the intended reaction is inhibited unpreferably.

The hydrocarboxylation or hydroesterification reaction is carried out at a reaction temperature of 40° to 250° C., preferably 70° to 120° C. When the reaction temperature is less than 40° C., a reaction rate is too low to actually achieve the hydroformylation. When it is more than 250° C., polymerization reaction and the decomposition of the complex catalyst occur unpreferably.

The pressure of carbon monoxide is 10 kg/cm$^2$ or more. When the pressure is less than 10 kg/cm$^2$, a reaction rate is too low to actually achieve the hydrocarboxylation or hydroesterification reaction. The higher the pressure of carbon monoxide is, the faster the reaction proceeds, but when the pressure is too high, it is required to sufficiently heighten the pressure resistance of a reactor. Therefore, it is natural that the upper limit of the reaction pressure is present, and it is 600 kg/cm$^2$ or less in practice.

The reaction is allowed to proceed until carbon monoxide is not absorbed any more, and the reaction time is usually in the range of 4 to 20.hours.

Examples of the usable alcohol include lower alcohols having 1 to 4 carbon atoms such as methyl alcohol, ethyl alcohol, n-propyl alcohol, isopropyl alcohol, n-butyl alcohol, sec-butyl alcohol and isobutyl alcohol, and above all, methyl alcohol is preferable.

After completion of the hydrocarboxylation or hydroesterification reaction, the resultant reaction product can be easily separated into desired high-purity α-(4-isobutylphenyl)propionic acid or its alkyl ester and the catalyst by extraction or distillation. The thus recovered complex catalyst can be reused.

The alkyl α-(4-isobutylphenyl)propionate obtained by the present invention is hydrolyzed in the presence of an acid or an alkali catalyst in a usual manner in order to be easily converted into α-(4-isobutylphenyl)propionic acid.

Now, the present invention will be described in more detail in reference to examples and comparative examples

PREPARATION OF P-ISOBUTYLETHYLBENZENE [STEP(I)]

Examples 1 to 27

Isobutylbenzene and each polyalkylbenzene which was an alkylating agent were adjusted to predetermined concentrations, and reaction was then carried out in the presence of each acid catalyst on a batch system. Compositions of raw material oils, conditions of the reactions and the results are set forth in Tables 1, 2 and 3.

TABLE 1

| | Example 1 | Example 2 |
|---|---|---|
| Catalyst | HY Zeolite | HY Zeolite |
| Amount of Catalyst (pts. wt.) | 4.8 | 4.8 |
| Material Oil (pts. wt.) | 95.2 | 95.2 |
| Temp. (°C.) | 190 | 190 |
| Time (hr) | 24 | 24 |

| | Composition (%) | | | |
|---|---|---|---|---|
| | Material | Reaction Solution | Material | Reaction Solution |
| Benzene | — | 0.8 | — | 0.4 |
| Ethylbenzene | — | 15.3 | — | 6.1 |
| Isobutylbenzene | 49.3 | 32.2 | 50.6 | 18.1 |
| sec-Butylbenzene | — | 0.2 | — | 0.3 |
| Diethylbenzene | 50.7 | 26.5 | — | 20.1 |
| o-Isobutylethylbenzene | — | 0.4 | — | 0.5 |
| m-Isobutylethylbenzene | — | 8.5 | — | 13.3 |
| p-Isobutylethylbenzene | — | 10.1 | — | 18.2 |
| Triethylbenzene | — | 4.7 | 49.0 | 16.9 |
| Tetraethylbenzene | — | — | — | 0.2 |
| Pentaethylbenzene | — | — | — | — |
| Hexaethylbenzene | — | — | — | — |
| Others | — | 1.3 | 0.4 | 5.9 |
| Conversion of Isobutylbenzene (wt %) | 34.7 | | 64.1 | |
| Selectivity of p-Isobutylethylbenzene (mol %) | 48.7 | | 46.3 | |
| Isobutylethylbenzene (o/m/p) | 2/45/53 | | 1/42/57 | |

| | Example 3 | Example 4 |
|---|---|---|
| Catalyst | SiO$_2$/Al$_2$O$_3$ | SiO$_2$/Al$_2$O$_3$ |
| Amount of Catalyst (pts. wt.) | 4.8 | 4.8 |
| Material Oil (pts. wt.) | 95.2 | 95.2 |
| Temp. (°C.) | 250 | 300 |
| Time (hr) | 8 | 8 |

TABLE 1-continued

| | Composition (%) | | |
|---|---|---|---|
| | Material | Reaction Solution | Reaction Solution |
| Benzene | — | — | 2.1 |
| Ethylbenzene | — | 0.4 | 4.7 |
| Isobutylbenzene | 52.6 | 47.4 | 25.4 |
| sec-Butylbenzene | — | 0.6 | 1.5 |
| Diethylbenzene | 6.4 | 8.4 | 16.2 |
| o-Isobutylethylbenzene | — | trace | 0.6 |
| m-Isobutylethylbenzene | — | 1.5 | 8.3 |
| p-Isobutylethylbenzene | — | 2.7 | 7.3 |
| Triethylbenzene | 32.2 | 30.2 | 20.9 |
| Tetraethylbenzene | 7.5 | 6.7 | 2.5 |
| Pentaethylbenzene | — | — | — |
| Hexaethylbenzene | — | — | — |
| Others | 1.3 | 2.1 | 10.5 |
| Conversion of Isobutylbenzene (wt %) | 9.9 | | 51.7 |
| Selectivity of p-Isobutylethylbenzene (mol %) | 42.9 | | 22.2 |
| Isobutylethylbenzene (o/m/p) | 0/36/64 | | 4/51/45 |

| | Example 5 | Example 6 |
|---|---|---|
| Catalyst | HY Zeolite | HY Zeolite |
| Amount of Catalyst (pts. wt.) | 4.8 | 4.8 |
| Material Oil (pts. wt.) | 95.2 | 95.2 |
| Temp. (°C.) | 160 | 170 |
| Time (hr) | 9 | 14 |

| | Composition (%) | | |
|---|---|---|---|
| | Material | Reaction Solution | Reaction Solution |
| Benzene | — | — | 0.3 |
| Ethylbenzene | — | 2.4 | 5.7 |
| Isobutylbenzene | 52.6 | 31.4 | 21.3 |
| sec-Butylbenzene | — | 0.2 | 0.2 |
| Diethylbenzene | 6.4 | 14.1 | 18.1 |
| o-Isobutylethylbenzene | — | 0.3 | 0.5 |
| m-Isobutylethylbenzene | — | 7.0 | 11.7 |
| p-Isobutylethylbenzene | — | 15.2 | 19.5 |
| Triethylbenzene | 32.2 | 24.3 | 16.8 |
| Tetraethylbenzene | 7.5 | 2.5 | 0.7 |
| Pentaethylbenzene | — | — | — |
| Hexaethylbenzene | — | — | — |
| Others | 1.3 | 2.6 | 5.2 |
| Conversion of Isobutylbenzene (wt %) | 40.3 | | 59.5 |
| Selectivity of p-Isobutylethylbenzene | 59.3 | | 51.5 |

TABLE 1-continued

|  |  |  |
|---|---|---|
| (mol %) |  |  |
| Isobutyl-ethylbenzene (o/m/p) | 1/31/68 | 1/37/62 |

|  | Example 7 | Example 8 | Example 9 |
|---|---|---|---|
| Catalyst | HY Zeolite | HY Zeolite | HY Zeolite |
| Amount of Catalyst (pts. wt.) | 4.8 | 4.8 | 4.8 |
| Material Oil (pts. wt.) | 95.2 | 95.2 | 95.2 |
| Temp. (°C.) | 180 | 190 | 202 |
| Time (hr) | 7 | 5 | 2 |

|  | Composition (%) | | |
|---|---|---|---|
|  | Reaction Solution | Reaction Solution | Reaction Solution |
| Benzene | 0.2 | 0.3 | 0.2 |
| Ethylbenzene | 5.4 | 6.0 | 5.2 |
| Isobutyl-benzene | 18.2 | 17.4 | 19.7 |
| sec-Butyl-benzene | 0.2 | 0.3 | 0.3 |
| Diethyl-benzene | 18.6 | 19.1 | 18.3 |
| o-Isobutyl-ethylbenzene | 0.5 | 0.6 | 0.5 |
| m-Isobutyl-ethylbenzene | 14.0 | 14.6 | 13.4 |
| p-Isobutyl-ethylbenzene | 19.6 | 18.7 | 17.7 |
| Triethyl-benzene | 15.9 | 15.0 | 17.0 |
| Tetraethyl-benzene | 0.5 | 0.4 | 0.8 |
| Pentaethyl-benzene | — | — | — |
| Hexaethyl-benzene | — | — | — |
| Others | 6.9 | 7.6 | 6.9 |
| Conversion of Isobutyl-benzene (wt %) | 65.4 | 66.8 | 62.5 |
| Selectivity of p-Isobutyl-ethylbenzene (mol %) | 47.2 | 44.0 | 44.6 |
| Isobutyl-ethylbenzene (o/m/p) | 2/41/57 | 2/43/55 | 2/42/56 |

|  | Example 10 | | Example 11 | |
|---|---|---|---|---|
| Catalyst | HY Zeolite | | HY Zeolite | |
| Amount of Catalyst (pts. wt.) | 4.8 | | 4.8 | |
| Material Oil (pts. wt.) | 95.2 | | 95.2 | |
| Temp. (°C.) | 180 | | 180 | |
| Time (hr) | 7 | | 14 | |

|  | Composition (%) | | | |
|---|---|---|---|---|
|  | Material | Reaction Solution | Material | Reaction Solution |
| Benzene | — | 0.5 | — | — |
| Ethylbenzene | — | 5.9 | — | 3.4 |
| Isobutyl-benzene | 70.5 | 35.1 | 37.7 | 7.9 |
| sec-Butyl-benzene | — | 0.8 | — | 0.3 |
| Diethyl-benzene | 5.3 | 9.6 | 10.9 | 15.8 |
| o-Isobutyl-ethylbenzene | — | 0.8 | — | 0.3 |
| m-Isobutyl-ethylbenzene | — | 13.6 | — | 8.7 |
| p-Isobutyl-ethylbenzene | — | 18.9 | — | 19.0 |
| Triethyl-benzene | 5.9 | 6.7 | 12.4 | 23.9 |
| Tetraethyl-benzene | 6.0 | 0.8 | 12.7 | 9.3 |
| Pentaethyl-benzene | 6.5 | — | 13.6 | 0.5 |
| Hexaethyl-benzene | 1.9 | — | 3.9 | 0.9 |
| Others | 3.9 | 7.3 | 8.8 | 10.0 |
| Conversion of Isobutyl-benzene (wt %) | 50.2 | | 79.0 | |
| Selectivity of p-Isobutyl-ethylbenzene (mol %) | 44.2 | | 52.7 | |
| Isobutyl-ethylbenzene (o/m/p) | 2/41/57 | | 1/31/68 | |

TABLE 2

|  | Example 12 | Example 13 |
|---|---|---|
| Catalyst | HY Zeolite | HY Zeolite |
| Amount of Catalyst (pts. wt.) | 4.8 | 4.8 |
| Material Oil (pts. wt.) | 95.2 | 95.2 |
| Temp. (°C.) | 170 | 180 |
| Time (hr) | 8 | 5 |

|  | Composition (%) | | |
|---|---|---|---|
|  | Material | Reaction Solution | Reaction Solution |
| Benzene | — | 0.2 | 0.2 |
| Toluene | — | 4.0 | 4.0 |
| Ethylbenzene | — | 0.9 | 1.3 |
| Xylene | — | 0.6 | 0.7 |
| Ethyltoluene | 15.6 | 15.6 | 15.9 |
| Isobutyl-benzene | 54.0 | 24.4 | 22.0 |
| sec-Butyl-benzene | — | 0.3 | 0.5 |
| Diethyl-benzene | — | 1.8 | 2.3 |
| Diethyl-toluene | 11.5 | 14.1 | 13.5 |
| o-Isobutyl-ethylbenzene | — | 0.6 | 0.7 |
| m-Isobutyl-ethylbenzene | — | 10.0 | 11.3 |
| p-Isobutyl-ethylbenzene | — | 17.4 | 16.8 |
| Triethyl-toluene | 6.8 | 1.9 | 1.2 |
| Tetraethyl-toluene | 6.3 | — | — |
| Pentaethyl-toluene | 1.9 | — | — |
| Others | 3.9 | 8.2 | 9.6 |
| Conversion of Isobutyl-benzene (wt %) | 54.8 | | 59.3 |
| Selectivity of p-Isobutyl-ethylbenzene (mol %) | 48.6 | | 43.4 |
| Isobutyl-ethylbenzene (o/m/p) | 2/36/62 | | 3/39/58 |

|  | Example 14 | Example 15 |
|---|---|---|
| Catalyst | HY Zeolite | HY Zeolite |
| Amount of Catalyst (pts. wt.) | 4.8 | 4.8 |

TABLE 2-continued

|  | | |
|---|---|---|
| Material Oil (pts. wt.) | 95.2 | 95.2 |
| Temp. (°C.) | 190 | 200 |
| Time (hr) | 3 | 1 |

| Composition (%) | Reaction Solution | Reaction Solution |
|---|---|---|
| Benzene | 0.3 | 0.2 |
| Toluene | 4.1 | 3.7 |
| Ethylbenzene | 1.4 | 1.1 |
| Xylene | 0.7 | 0.5 |
| Ethyltoluene | 15.7 | 15.2 |
| Isobutylbenzene | 22.6 | 25.2 |
| sec-Butylbenzene | 0.4 | 0.5 |
| Diethylbenzene | 2.7 | 1.9 |
| Diethyltoluene | 13.6 | 14.8 |
| o-Isobutylethylbenzene | 0.7 | 0.6 |
| m-Isobutylethylbenzene | 11.0 | 9.8 |
| p-Isobutylethylbenzene | 16.1 | 15.3 |
| Triethyltoluene | 1.4 | 2.3 |
| Tetraethyltoluene | — | — |
| Pentaethyltoluene | — | — |
| Others | 9.3 | 8.9 |
| Conversion of Isobutylbenzene (wt %) | 58.1 | 53.3 |
| Selectivity of p-Isobutylethylbenzene (mol %) | 42.4 | 43.9 |
| Isobutylethylbenzene (o/m/p) | 2/40/58 | 2/38/60 |

|  | Example 16 | | Example 17 | |
|---|---|---|---|---|
| Catalyst | HY Zeolite | | HY Zeolite | |
| Amount of Catalyst (pts. wt.) | 4.8 | | 4.8 | |
| Material Oil (pts. wt.) | 95.2 | | 95.2 | |
| Temp. (°C.) | 170 | | 170 | |
| Time (hr) | 6 | | 12 | |

| Composition (%) | Material | Reaction Solution | Material | Reaction Solution |
|---|---|---|---|---|
| Benzene | — | 0.4 | — | — |
| Toluene | — | 4.1 | — | 3.2 |
| Ethylbenzene | — | 1.0 | — | 0.8 |
| Xylene | — | — | — | 0.6 |
| Ethyltoluene | 7.6 | 8.5 | 21.0 | 17.9 |
| Isobutylbenzene | 77.8 | 53.3 | 36.6 | 12.0 |
| sec-Butylbenzene | — | 0.6 | — | 0.2 |
| Diethylbenzene | — | 0.7 | — | 2.5 |
| Diethyltoluene | 5.3 | 4.7 | 16.3 | 22.4 |
| o-Isobutylethylbenzene | — | 0.6 | — | 0.7 |
| m-Isobutylethylbenzene | — | 9.4 | — | 7.6 |
| p-Isobutylethylbenzene | — | 12.4 | — | 15.3 |
| Triethyltoluene | 3.2 | 0.2 | 9.4 | 5.0 |
| Tetraethyltoluene | 3.0 | — | 8.4 | — |
| Pentaethyltoluene | 0.9 | — | 2.5 | — |
| Others | 2.2 | 4.1 | 5.8 | 11.8 |
| Conversion of Isobutylbenzene (wt %) |  | 31.5 |  | 67.2 |
| Selectivity of p-Isobutylethylbenzene (mol %) |  | 41.9 |  | 51.4 |
| Isobutylethylbenzene (o/m/p) |  | 3/42/55 |  | 3/32/65 |

|  | Example 18 | | Example 19 | |
|---|---|---|---|---|
| Catalyst | HY Zeolite | | HY Zeolite | |
| Amount of Catalyst (pts. wt.) | 4.8 | | 4.8 | |
| Material Oil (pts. wt.) | 95.2 | | 95.2 | |
| Temp. (°C.) | 170 | | 170 | |
| Time (hr) | 6 | | 17 | |

| Composition (%) | Material | Reaction Solution | Material | Reaction Solution |
|---|---|---|---|---|
| Benzene | — | 0.3 | — | — |
| Toluene | — | 4.1 | — | 2.5 |
| Ethylbenzene | — | 1.0 | — | 0.8 |
| Xylene | — | 0.3 | — | 0.7 |
| Ethyltoluene | 10.2 | 11.3 | 23.7 | 18.3 |
| Isobutylbenzene | 69.8 | 42.6 | 27.6 | 7.2 |
| sec-Butylbenzene | — | 0.5 | — | 0.2 |
| Diethylbenzene | — | 1.1 | — | 3.0 |
| Diethyltoluene | 7.7 | 7.1 | 18.4 | 27.6 |
| o-Isobutylethylbenzene | — | 0.6 | — | 0.7 |
| m-Isobutylethylbenzene | — | 10.2 | — | 6.1 |
| p-Isobutylethylbenzene | — | 15.2 | — | 12.8 |
| Triethyltoluene | 4.5 | 0.5 | 10.7 | 7.2 |
| Tetraethyltoluene | 4.0 | — | 9.5 | 0.2 |
| Pentaethyltoluene | 1.2 | — | 2.6 | — |
| Others | 2.6 | 5.2 | 7.5 | 12.7 |
| Conversion of Isobutylbenzene (wt %) |  | 39.0 |  | 73.9 |
| Selectivity of p-Isobutylethylbenzene (mol %) |  | 46.2 |  | 51.9 |
| Isobutylethylbenzene (o/m/p) |  | 3/39/58 |  | 4/31/65 |

TABLE 3

|  | Example 20 | Example 21 |
|---|---|---|
| Catalyst | AlCl$_3$ | AlCl$_3$ |
| Amount of Catalyst (pts. wt.) | 2.9 | 2.9 |
| Material Oil (pts. wt.) | 97.1 | 97.1 |
| Temp. (°C.) | 40 | 60 |
| Time (hr) | 5 | 1 |

TABLE 3-continued

|  | Composition (%) | | |
| --- | --- | --- | --- |
|  | Material | Reaction Solution | Reaction Solution |
| Benzene | — | 0.1 | 0.2 |
| Toluene | — | 5.0 | 6.1 |
| Ethylbenzene | — | 0.6 | 1.1 |
| Xylene | — | trace | trace |
| Ethyltoluene | 20.0 | 17.7 | 18.0 |
| Isobutylbenzene | 52.9 | 33.5 | 28.4 |
| sec-Butylbenzene | — | — | — |
| Diethylbenzene | — | 0.7 | 1.2 |
| Diethyltoluene | 8.5 | 9.6 | 9.7 |
| o-Isobutylethylbenzene | — | 0.6 | 0.8 |
| m-Isobutylethylbenzene | — | 5.2 | 8.1 |
| p-Isobutylethylbenzene | — | 16.5 | 16.3 |
| Triethyltoluene | 4.6 | 1.3 | 0.6 |
| Tetraethyltoluene | 3.7 | — | — |
| Pentaethyltoluene | 1.2 | 0.7 | 0.3 |
| Others | 9.1 | 8.5 | 9.2 |
| Conversion of Isobutylbenzene (wt %) |  | 36.7 | 46.5 |
| Selectivity of p-Isobutylethylbenzene (mol %) |  | 70.4 | 54.8 |
| Isobutylethylbenzene (o/m/p) |  | 3/23/74 | 3/32/65 |

|  | Example 22 | Example 23 |
| --- | --- | --- |
| Catalyst | CF$_3$SO$_3$H | HF |
| Amount of Catalyst (pts. wt.) | 4.8 | 4.7 |
| Material Oil (pts. wt.) | 95.2 | 95.3 |
| Temp. (°C.) | 120 | 120 |
| Time (hr) | 6 | 3 |

|  | Composition (%) | | |
| --- | --- | --- | --- |
|  | Material | Reaction Solution | Reaction Solution |
| Benzene | — | — | — |
| Toluene | — | 3.6 | 3.2 |
| Ethylbenzene | — | 0.4 | 0.3 |
| Xylene | — | trace | trace |
| Ethyltoluene | 20.0 | 17.9 | 17.4 |
| Isobutylbenzene | 36.3 | 19.7 | 22.9 |
| sec-Butylbenzene | — | — | — |
| Diethylbenzene | 0.8 | 1.1 | 1.0 |
| Diethyltoluene | 11.8 | 19.0 | 18.6 |
| o-Isobutylethylbenzene | — | 0.9 | 0.8 |
| m-Isobutylethylbenzene | — | 4.3 | 3.7 |
| p-Isobutylethylbenzene | — | 14.4 | 12.2 |
| Triethyltoluene | 7.1 | 4.8 | 5.5 |
| Tetraethyltoluene | 5.7 | 0.6 | 1.1 |
| Pentaethyltoluene | 3.1 | 1.0 | 1.5 |
| Others | 15.2 | 12.3 | 11.8 |
| Conversion of Isobutylbenzene (wt %) |  | 45.7 | 36.9 |
| Selectivity of p-Isobutylethylbenzene (mol %) |  | 71.8 | 75.3 |
| Isobutylethylbenzene (o/m/p) |  | 5/22/73 | 5/22/73 |

|  | Example 24 | Example 25 |
| --- | --- | --- |
| Catalyst | Phosphotungstic acid | HX Zeolite |
| Amount of Catalyst (pts. wt.) | 4.8 | 4.8 |
| Material Oil (pts. wt.) | 95.2 | 95.2 |
| Temp. (°C.) | 300 | 180 |
| Time (hr) | 6 | 6 |

|  | Composition (%) | | |
| --- | --- | --- | --- |
|  | Reaction Solution | Material | Reaction Solution |
| Benzene | — | — | 0.2 |
| Toluene | 2.5 | — | 4.1 |
| Ethylbenzene | 0.1 | — | 1.5 |
| Xylene | — | — | 0.8 |
| Ethyltoluene | 20.2 | 15.6 | 15.7 |
| Isobutylbenzene | 34.2 | 54.0 | 20.6 |
| sec-Butylbenzene | 0.5 | — | 0.5 |
| Diethylbenzene | 0.5 | — | 2.6 |
| Diethyltoluene | 12.0 | 11.5 | 13.0 |
| o-Isobutylethylbenzene | 0.5 | — | 0.7 |
| m-Isobutylethylbenzene | 1.6 | — | 11.9 |
| p-Isobutylethylbenzene | 1.1 | — | 16.5 |
| Triethyltoluene | 7.7 | 6.8 | 0.9 |
| Tetraethyltoluene | 6.8 | 6.3 | — |
| Pentaethyltoluene | 0.4 | 1.9 | — |
| Others | 11.9 | 3.9 | 11.6 |
| Conversion of Isobutylbenzene (wt %) | 5.8 |  | 61.9 |
| Selectivity of p-Isobutylethylbenzene (mol %) | 43.3 |  | 40.9 |
| Isobutylethylbenzene (o/m/p) | 16/50/34 |  | 2/41/57 |

|  | Example 26 | Example 27 |
| --- | --- | --- |
| Catalyst | H Faujasite | Nafion |
| Amount of Catalyst (pts. wt.) | 4.8 | 2.9 |
| Material Oil (pts. wt.) | 95.2 | 97.1 |
| Temp. (°C.) | 170 | 190 |
| Time (hr) | 6 | 12 |

|  | Composition (%) | |
| --- | --- | --- |
|  | Reaction Solution | Reaction Solution |
| Benzene | — | — |
| Toluene | 3.6 | 3.2 |
| Ethylbenzene | 0.7 | 0.5 |

TABLE 3-continued

| | | |
|---|---|---|
| Xylene | 0.3 | — |
| Ethyltoluene | 15.1 | 14.3 |
| Isobutylbenzene | 27.0 | 32.7 |
| sec-Butylbenzene | 0.3 | 0.3 |
| Diethylbenzene | 1.4 | 1.1 |
| Diethyltoluene | 14.9 | 15.3 |
| o-Isobutylethylbenzene | 0.6 | 0.6 |
| m-Isobutylethylbenzene | 8.9 | 6.4 |
| p-Isobutylethylbenzene | 16.9 | 13.5 |
| Triethyltoluene | 2.9 | 5.5 |
| Tetraethyltoluene | — | 0.8 |
| Pentaethyltoluene | — | — |
| Others | 7.4 | 5.8 |
| Conversion of Isobutylbenzene (wt %) | 50.0 | 39.4 |
| Selectivity of p-Isobutylethylbenzene (mol %) | 51.8 | 52.4 |
| Isobutylethylbenzene (o/m/p) | 2/34/64 | 3/31/66 |

EXAMPLES 28 to 31

A stainless steel pipe having an inner diameter of 12 mm and a length of 1 m was packed with 64 ml (35.2 g) of an HY zeolite catalyst (made by Shokubai Chemicals Co., Ltd.; grain diameter 2-3 mm), and the system in the pipe was replaced with nitrogen.

A mixed raw material oil comprising isobutylbenzene and a polyalkylbenzene of an alkylating agent and having a predetermined concentration was fed to the above-mentioned reactor at a flow rate of 16 ml/hr, and the temperature of the catalyst layer was maintained at a predetermined level in order to carry out reaction. Afterward, the resulting reaction mixture was analyzed through a gas chromatography. The composition of the mixed raw material oil, the conditions of the reaction and the results are set forth in Tables 4 and 5.

TABLE 4

| | Example 28 | | Example 29 | |
|---|---|---|---|---|
| Catalyst | HY Zeolite | | HY Zeolite | |
| LHSV (hr⁻¹) | 0.25 | | 0.25 | |
| Reaction Temp. (°C.) | 180 | | 180 | |
| Oil Feed Time (hr) | 24 | | 24 | |
| | Composition (%) | | | |
| | Material | Reaction Solution | Material | Reaction Solution |
| Benzene | — | 3.6 | — | 0.6 |
| Ethylbenzene | — | 21.3 | — | 5.1 |
| Isobutylbenzene | 49.9 | 20.1 | 54.2 | 19.0 |
| sec-Butylbenzene | — | 0.6 | — | 0.6 |
| Diethylbenzene | 49.9 | 18.9 | 7.9 | 14.2 |
| o-Isobutylethylbenzene | — | 0.7 | — | 0.6 |
| m-Isobutylethylbenzene | — | 13.3 | — | 12.9 |
| p-Isobutylethylbenzene | — | 9.2 | — | 18.3 |
| Triethylbenzene | — | 3.7 | 9.2 | 13.4 |
| Tetraethylbenzene | — | — | 9.6 | 4.2 |
| Pentaethylbenzene | — | — | 10.2 | — |
| Hexaethylbenzene | — | — | 2.9 | — |
| Others | 0.2 | 8.6 | 6.0 | 11.1 |
| Conversion of Isobutylbenzene (wt %) | 59.7 | | 64.9 | |
| Selectivity of p-Isobutylethylbenzene (mol %) | 25.5 | | 43.0 | |
| Isobutylethylbenzene (o/m/p) | 3/57/40 | | 1/41/58 | |

TABLE 5

| | Example 30 | | Example 31 | |
|---|---|---|---|---|
| Catalyst | HY Zeolite | | HY Zeolite | |
| LHSV (hr⁻¹) | 0.25 | | 0.25 | |
| Reaction Temp. (°C.) | 180 | | 190 | |
| Oil Feed Time (hr) | 24 | | 24 | |
| | Composition (%) | | | |
| | Material | Reaction Solution | Material | Reaction Solution |
| Benzene | — | — | — | 0.1 |
| Toluene | — | 3.2 | — | 2.3 |
| Ethylbenzene | — | 0.4 | — | 0.3 |
| Xylene | — | — | — | 0.1 |
| Ethyltoluene | 15.6 | 14.1 | 9.5 | 10.2 |
| Isobutylbenzene | 54.0 | 35.7 | 55.3 | 33.1 |
| sec-Butylbenzene | — | 0.3 | — | 0.3 |
| Diethylbenzene | — | 0.8 | — | 0.8 |
| Diethyltoluene | 11.5 | 14.5 | 12.7 | 14.7 |
| o-Isobutylethylbenzene | — | 0.6 | — | 0.6 |
| m-Isobutylethylbenzene | — | 6.0 | — | 5.6 |
| p-Isobutylethylbenzene | — | 11.9 | — | 12.4 |
| Triethyltoluene | 6.8 | 6.3 | 8.1 | 9.9 |
| Tetraethyltoluene | 6.3 | 1.1 | 9.1 | 2.6 |
| Pentaethyltoluene | 1.9 | — | 3.6 | 0.3 |
| Others | 3.9 | 5.1 | 1.7 | 6.7 |
| Conversion of Isobutylbenzene (wt %) | 33.9 | | 40.1 | |
| Selectivity of p-Isobutylethylbenzene (mol %) | 53.8 | | 46.2 | |
| Isobutylethylbenzene (o/m/p) | 4/32/64 | | 3/30/67 | |

EXAMPLE 32

In a 15-liter three-necked flask was placed 10 kg of the reaction mixture obtained in Example 31, and a glass pipe having an inner diameter of 30 mm and a length of 1.5 m was packed with a filler, Heli Pack No. 3 metal made by Tokyo Tokushu Kanaami Co., Ltd. Afterward, distillation was carried out on a batch system by the use of a distillation column in which the number of theoretical plates was 35, and in this case, a fraction of p-isobutylethylbenzene having a purity of 97% or more by weight was prepared in an amount of 997 g (recovery 80.4%).

PREPARATION OF P-ISOBUTYLSTYRENE [STEP (II)]

Experimental Example 33

The promotors of potassium and chromium as well as the dehydrogenation catalyst of iron oxide (trade name G-64A; made by Nissan Gardlar Co., Ltd.) were ground so that a grain diameter might be in the range of from 1 to 2 mm, and a stainless steel pipe having an inner diameter of 12 mm and a length of 1 m was packed with 20 ml of the resulting powder.

p-Isobutylethylbenzene (hereinafter referred to a "PBE" sometimes) and water were passed, at flow rates of 10 ml/hr and 90 ml/hr, respectively, through a preheater pipe and the catalyst layer in the pipe at a temperature of 550° C., so that dehydrogenation was carried out (a contact time with the catalyst=0.2 second; the molar ratio of steam to p-isobutylethylbenzene=93). The dehydrogenated material was then cooled, and a gas and water were separated and removed therefrom. Afterward, the resultant organic phase was analyzed by a gas chromatography in order to inspect the conversion of p-isobutylethylbenzene and the selectivity of p-isobutylstyrene (hereinafter referred to as "PBS" at times).

It was confirmed that the organic phase of the dehydrogenated substance was mainly composed of PBE, PBS, 4-(2'-methyl-1'-propenyl)ethylbenzene (hereinafter referred to as "1-MPE" sometimes), 4-(2'-methyl-2'-propenyl)ethylbenzene (hereinafter referred to as "2-MPE" sometimes), 4-(2'-methyl-1'-propenyl)vinylbenzene (hereinafter referred to as "1-MPV" sometimes) and 4-(2'-methyl-2'-propenyl)vinylbenzene (hereinafter referred to as "2-MPV" sometimes). The composition of the organic phase is set forth in Table 6.

TABLE 6

| Component | Content |
|---|---|
| PBE | 69.3% by weight |
| PBS | 24.7% by weight |
| 1-MPE | 0.6% by weight |
| 2-MPE | 1.6% by weight |
| 1-MPV | 0.9% by weight |
| 2-MPV | 2.1% by weight |
| Unidentified | 0.8% by weight |

From these data, it is apparent that the conversion of PBE was 31% and the selectivity of PBS was 83%, and it was confirmed that PBS was formed in the high selectivity by the dehydrogenation.

Afterward, the dehydrogenated material was separated into constitutional components, and they were analyzed by means of mass spectrometry, infrared spectrophotometry and NMR. As a result, p-isobutylethylbenzene was identical with that which was used as the raw material, and the production of sec-butylbenzene and tert-butylbenzene was not perceived. In other words, it could be confirmed that secondary reactions such as the isomerization of an isobutyl group did not occur, and that the butyl group in PBS is an isobutyl group and this group was present at the p-position.

Experimental Examples 34 to 37

Following the same procedure as in Experimental Example 33, dehydrogenation was carried out, changing reaction temperatures. The obtained results are set forth together with the results of Experimental Example 33 in Table 7.

TABLE 7

| | Experimental Example No. | | | | |
|---|---|---|---|---|---|
| | 34 | 35 | 33 | 36 | 37 |
| Reaction Temp. (°C.) | 450 | 500 | 550 | 600 | 650 |
| Contact Time (sec) | 0.2 | 0.2 | 0.2 | 0.2 | 0.2 |
| Molar Ratio of Steam | 93 | 94 | 92 | 93 | 94 |
| Conversion of PBE (%) | 1 | 6 | 31 | 75 | 96 |
| Selectivity of PBS (%) | 99 | 98 | 83 | 51 | 7 |

Experimental Examples 38 to 42

Following the same procedure as in Experimental Example 33, dehydrogenation reaction was carried out, changing each contact time. The results are set forth in Table 8.

TABLE 8

| | Experimental Example No. | | | | |
|---|---|---|---|---|---|
| | 38 | 39 | 40 | 41 | 42 |
| Reaction Temp. (°C.) | 550 | 550 | 550 | 550 | 550 |
| Contact Time (sec) | 0.06 | 0.10 | 0.21 | 0.28 | 0.38 |
| Molar Ratio of Steam | 96 | 98 | 96 | 94 | 96 |
| Conversion of PBE (%) | 21 | 33 | 37 | 47 | 54 |
| Selectivity of PBS (%) | 89 | 84 | 79 | 73 | 69 |

Experimental Examples 43 to 47

Following the same procedure as in Experimental Example 33, dehydrogenation reaction was carried out, using a copper-chromium dehydrogenation catalyst comprising 43% by weight of CuO, 42% by weight of $Cr_2O_3$ and 15% by weight of $SiO_2$, each reaction temperature being changed. The results are set forth in Table 9.

TABLE 9

| | Experimental Example No. | | | | |
|---|---|---|---|---|---|
| | 43 | 44 | 45 | 46 | 47 |
| Reaction Temp. (°C.) | 450 | 500 | 550 | 600 | 650 |
| Contact Time (sec) | 0.2 | 0.2 | 0.2 | 0.2 | 0.2 |
| Molar Ratio of Steam | 93 | 94 | 92 | 93 | 94 |
| Conversion of PBE (%) | 5 | 8 | 20 | 50 | 92 |
| Selectivity of PBS (%) | 80 | 79 | 74 | 58 | 5 |

Experimental Examples 48 to 52

Following the same procedure as in Experimental Example 33, dehydrogenation reaction was carried out, using a copper-chromium dehydrogenation catalyst comprising 18% by weight of $Cr_2O_3$, and 39% by weight of CuO and 38% by weight of ZnO. The results are set forth in Table 10.

TABLE 10

|  | Experimental Example No. | | | | |
|---|---|---|---|---|---|
|  | 48 | 49 | 50 | 51 | 52 |
| Reaction Temp. (°C.) | 450 | 500 | 550 | 600 | 650 |
| Contact Time (sec) | 0.2 | 0.2 | 0.2 | 0.2 | 0.2 |
| Molar Ratio of Steam | 93 | 93 | 94 | 93 | 93 |
| Conversion of PBE (%) | 2 | 6 | 12 | 21 | 45 |
| Selectivity of PBS (%) | 78 | 76 | 72 | 64 | 47 |

Experimental Example 53

Following the same procedure as in Experimental Example 33, dehydrogenation reaction of PBE was carried out, changing each metal of the dehydrogenation metal catalyst as in the following table. All of the metals were used in the form of oxides, and each metal was supported in silica. The results are set forth in the following table.

| Metal | Conversion (%) | Selectivity (%) |
|---|---|---|
| Ag | 31 | 62 |
| Cd | 12 | 64 |
| Cr | 22 | 61 |
| Zn | 13 | 52 |
| Mo | 16 | 53 |
| W | 11 | 59 |
| Mn | 11 | 61 |
| Tc | 12 | 60 |
| Re | 20 | 57 |
| Ru | 17 | 68 |
| Os | 12 | 70 |
| Co | 21 | 59 |
| Rh | 32 | 48 |
| Ir | 25 | 51 |
| Ni | 48 | 41 |
| Pd | 46 | 43 |
| Pt | 44 | 40 |

HYDROFORMYLATION STEP [STEP (IIIa)]

Experimental Example 54

In a 100-ml autoclave equipped with a stirrer were placed 30 g of p-isobutylstyrene having 97.8% by weight purity obtained by distilling/purifying the organic phase of the dehydrogenated material prepared in Experimental Example 33 and 0.3 g of rhodium hydridocarbonyltristriphenylphosphine. The temperature in the autoclave was then elevated up to 60° C. with stirring, and the pressure therein was increased to 50 kg/cm$^2$ by an equimolar mixed gas of hydrogen and carbon monoxide. Afterward, reaction was performed until the mixed gas had not been absorbed any more.

After completion of the reaction, the reaction mixture was cooled to room temperature, and was then analyzed by a gas chromatography. As a result, it was confirmed that the conversion of p-isobutylstyrene was 99.9% and the selectivity of α(4-isobutylphenyl)propionaldehyde was 88.7%.

Experimental Example 55

Following the same procedure as in Experimental Example 54 with the exception that rhodium hydridocarbonyltristriphenylphosphine was replaced with 0.1 g of rhodium oxide and 0.6 g of triphenylphosphine, experiment was carried out. As a result, the conversion of p-isobutylstyrene was 99.9%, and the selectivity of α-(4-isobutylphenyl)propionaldehyde was 82.2%.

Experimental Example 56

In a 200-ml autoclave equipped with a stirrer were placed 121.5 g of the organic phase of the dehydrogenated material obtained in Experimental Example 33 and 0.3 g of rhodium hydride carbonyltristriphenylphosphine, and the same procedure as in Experimental Example 54 was repeated. As a result, the conversion of p-isobutylstyrene was 99.8%, the selectivity of α-(4-isobutylphenyl)propionaldehyde was 87.8%, the hydroformylation of the substituted propenyl group of 4-(2'-methyl-1'-propenyl)ethylbenzene was 0%, the hydroformylation of the substituted propenyl group of 4-(2'-methyl-2'-propenyl)ethylbenzene was 0.4%, the hydroformylation of the substituted propenyl group of 4-(2'-methyl-1'-propenyl)vinylbenzene was 0%, and the hydroformylation of the substituted propenyl group of 4-(2'-methyl-2'-propenyl)vinylbenzene was 0.1%.

As described above, the carbon-carbon double bond of the substituted propenyl group is difficult to be carbonylated, and therefore the dehydrogenated reaction oil can be carbonylated directly as it is, as in this example.

PREPARATION OF α-(4-ISOBUTYLPHENYL)PROPIONIC ACID BY OXIDATION OF α-(4-ISOBUTYLPHENYL)PROPIONALDEHYDE

Experimental Example 57

In a 100-ml flask equipped with a stirrer was placed 10 g of α-(4-isobutylphenyl)propionaldehyde having a boiling point of 70° to 76° C./3 mmHg obtained by distilling the reaction mixture of Experimental Example 56 under reduced pressure, and 0.4 g of concentrated hydrochloric acid and 16 ml of acetone as a solvent were further added thereto. Afterward, the mixture was cooled to −15° C. Next, while the temperature of the mixture was maintained in the range of from −12° to −16° C., 36 g of a 10% aqueous sodium hypochlorite solution was gradually added dropwise thereto. After completion of the addition, reaction was further performed for 1 hour with stirring. After the reaction had been over, the mixture was neutralized with a 5% aqueous sodium hydroxide solution, so that its pH was adjusted to 8.5. The mixture was then allowed to stand, and the resultant lower layer, i.e., water phase was washed with normal hexane. Afterward, a 5% hydrochloric acid solution was added to the water phase in order to adjust its pH to 2, and a separated oil phase was then extracted with normal hexane and washed with water. Normal hexane was vaporized and removed under reduced pressure, thereby obtaining 9.3 g of light yellow crude α-(4-isobutylphenyl)propionic acid crystals.

Crude α-(4-isobutylphenyl)propionic acid was then recrystallized with a normal hexane solvent in order to obtain 7.5 g of white purified α-(4-isobutylphenyl)propionic acid (melting point=75°–76° C.). Spectra and the like of this product were in accord with the standards.

HYDROESTERIFICATION AND HYDROCARBOXYLATION STEP [STEP (IIIb)]

Experimental Example 58

Hydrocarboxylation

In a 500-ml autoclave were placed 50 g of p-isobutylstyrene having 97.8% by weight purity obtained by distilling/purifying the organic phase of the dehydrogenated material prepared in Experimental Example 33, 5.5 g of bisdichlorotriphenylphosphine palladium, 80 g of a 10% aqueous hydrochloric acid solution and 80 ml of toluene as a solvent. Afterward, the pressure in the autoclave was increased up to 100 kg/cm$^2$ at ordinary temperature with stirring by the use of carbon monoxide, and while the temperature in the autoclave was elevated up to 120° C., the pressure therein was further increased up to 300 kg/cm$^2$. After reaction proceeded and carbon monoxide had not been absorbed any more, the reaction was further continued for 24 hours.

After completion of the reaction, cooling followed in order to recover the reaction mixture, and the resultant oil layer and water layer were separated from each other by a separating funnel. The oil layer was then subjected to extraction three times by the use of 50 ml of a 8% aqueous sodium hydroxide solution, and an extracted aqueous solution was then mixed with the separated water layer. Hydrochloric acid was then added thereto so as to adjust the pH of the solution to 2. Afterward, extraction was performed three times with 500 ml of chloroform, and chloroform was then distilled off from the extract under reduced pressure, thereby obtaining 52.3 g of light yellow α-(4-isobutylphenyl)propionic acid crystals. In this case, the conversion of p-isobutylstyrene was 100%, and the selectivity coefficient of α-(4-isobutylphenyl)propionic acid was 89.0%.

Experimental Example 59

In a 500-ml autoclave were placed 202.43 g of the organic phase of the dehydrogenated material obtained in Experimental Example 33, 5.5 g of bisdichlorotriphenylphosphine palladium and 80 g of a 10% aqueous hydrochloric acid solution. Afterward, the pressure in the autoclave was increased up to 100 kg/cm$^2$ at ordinary temperature with stirring by the use of carbon monoxide, and while the temperature in the autoclave was elevated up to 120° C., the pressure therein was further increased up to 300 kg/cm$^2$ After reaction proceeded and carbon monoxide had not been absorbed any more, the reaction was further continued for 24 hours.

After completion of the reaction, cooling followed in order to recover the reaction mixture, and the resultant oil layer and water layer were separated from each other by a separating funnel. The oil layer was then subjected to extraction three times by the use of 50 ml of a 8% aqueous sodium hydroxide solution, and an extracted aqueous solution was then mixed with the separated water layer. Hydrochloric acid was then added thereto so as to adjust the pH of the solution to 2. Afterward, extraction was performed three times with 500 ml of chloroform, and chloroform was then distilled off from the extract under reduced pressure, thereby obtaining 50.2 g of light yellow α-(4-isobutylphenyl)propionic acid crystals. In this case, the conversion of p-isobutylstyrene was 100%, the selectivity coefficient of α-(4-isobutylphenyl)propionic acid was 87.3%, the hydrocarboxylation of the substituted propenyl group of 4-(2'-methyl-1'-propenyl)ethylbenzene was the hydrocarboxylation of the substituted propenyl group of 4-(2'-methyl-2'-propenyl)ethylbenzene was 0.8%, the hydrocarboxylation of the substituted propenyl group of 4-(2'-methyl-1'-propenyl)vinylbenzene was 0%, and the hydrocarboxylation of the substituted propenyl group of 4-(2'-methyl-2'-propenyl)vinylbenzene was 0.6%.

Experimental Example 60

Hydroesterification

In a 200-ml autoclave were placed 70.4 g of p-isobutylstyrene having 97.8% by weight purity obtained by distilling/purifying the organic phase of the dehydrogenated material prepared in Experimental Example 33, 25.5 ml of methanol, 40 ml of toluene as a solvent, 0.0756 g of PdCl$_2$ as a catalyst, 0.0292 g of CuCl$_2$ as a promotor and 0.2161 g of triphenylphosphine as a ligand. The temperature in the autoclave was then elevated up to 90° C. under stirring, and reaction was performed for 8 hours, while the pressure in the autoclave was maintained at 70 kg/cm$^2$ with carbon monoxide. After completion of the reaction, cooling followed, and the reaction mixture was then analyzed by means of a gas chromatography. As a result, the conversion of p-isobutylstyrene was 99.6%, the selectivity of methyl α-(4-isobutylphenyl)propionate was 90.9%.

Experimental Example 61

In a 500-ml autoclave were placed 285.0 g of the organic phase obtained in Experimental Example 33, 25.5 ml of methanol, 0.0756 g of PdCl$_2$ as a catalyst, 0.0292 g of CuCl$_2$ as a promotor and 0.2161 g of triphenylphosphine as a ligand. The temperature in the autoclave was then elevated up to 90° C. with stirring, and reaction was performed for 8 hours, while the pressure in the autoclave was maintained at 70 kg/cm$^2$ with carbon monoxide. After completion of the reaction, cooling followed, and the reaction mixture was then analyzed by means of a gas chromatography. As a result, the conversion of p-isobutylstyrene was 99.8%, the selectivity of methyl α-(4-isobutylphenyl)propionate was 88.9%, the hydroesterification of the substituted propenyl group of 4-(2'-methyl-1'-propenyl)ethylbenzene was 0%, the hydroesterification of the substituted propenyl group of 4-(2'-methyl-2'-propenyl)ethylbenzene was 0.6%, the hydroesterification of the substituted propenyl group of 4-(2'-methyl-1'-propenyl)vinylbenzene was 0%, and the hydroesterification of the substituted propenyl group of 4-(2'-methyl-2'-propenyl)vinylbenzene was 0.3%.

Preparation of α-(4-isobutylphenyl)propionic acid by hydrolyzing methyl α-(4-isobutylphenyl)propionate

Experimental Example 62

Thirty grams of methyl α-(4-isobutylphenyl)propionate in Experimental Example 60 and 150 ml of a 10% aqueous sodium hydroxide solution were refluxed with stirring for about 3 hours in order to perform hydrolysis. After cooling, the mixture was allowed to stand, and the separated lower layer, i.e., aqueous phase was then washed with normal hexane.

A 5% hydrochloric acid solution was added to the aqueous phase so as to adjust its pH to 2, and the separated oil was then extracted with normal hexane and washed with water. Afterward, normal hexane was vaporized/removed under reduced pressure, and thereby obtaining 23.9 g of light yellow crude α-(4-isobutylphenyl)propionic acid crystals.

Crude α-(4-isobutylphenyl)propionic acid was then recrystallized with a normal hexane solvent in order to obtain 20.7 g of white purified α-(4-isobutylphenyl)propionic acid (melting point=75°-76° C.). Spectra and the like of this product were in accord with the standards.

Experimental Example 63

One hundred grams of the hydroesterified reaction mixture in Experimental Example 61 and 150 ml of a 10% aqueous sodium hydroxide solution were refluxed with stirring for about 3 hours in order to perform hydrolysis. After cooling, the mixture was allowed to stand, and the separated lower layer, i.e., aqueous phase was then washed with normal hexane.

A 5% hydrochloric acid solution was added to the aqueous phase so as to adjust its pH to 2, and the separated oil was then extracted with normal hexane and washed with water. Afterward, normal hexane was vaporized/removed under reduced pressure, and thereby obtaining 22.4 g of light yellow crude α-(4-isobutylphenyl)propionic acid crystals.

Crude α-(4-isobutylphenyl)propionic acid was then recrystallized with a normal hexane solvent in order to obtain 19.9 g of white purified α-(4-isobutylphenyl)propionic acid (melting point=75°–76° C.). Spectra and the like of this product were in accord with the standards.

Comparative Examples 1 to 2

Isobutylbenzene and ethylbenzene were adjusted to predetermined concentrations, and reaction was then carried out on a batch system in the presence of an acid catalyst. The composition of each raw material oil, the conditions of the reaction and the results are set forth in Table 11.

As is apparent from the following Table 11, ethylbenzene is low in disproportionation activity, and therefore it is not desirable as an alkylating agent.

TABLE 11

|  | Comparative Example 1 | | Comparative Example 2 | |
| --- | --- | --- | --- | --- |
| Catalyst | HY Zeolite | | HY Zeolite | |
| Amount of Catalyst (pts. wt.) | 4.8 | | 4.8 | |
| Material Oil (pts. wt.) | 95.2 | | 95.2 | |
| Temp. (°C.) | 190 | | 200 | |
| Time (hr) | 24 | | 24 | |
| Composition (%) | | | | |
|  | Material | Reaction Solution | Material | Reaction Solution |
| Benzene | — | 3.1 | — | 5.0 |
| Ethylbenzene | 50.4 | 43.5 | 53.6 | 41.6 |
| Isobutylbenzene | 49.6 | 47.3 | 46.4 | 42.1 |
| sec-Butylbenzene | — | 0.2 | — | 0.4 |
| Diethylbenzene | — | 3.1 | — | 5.4 |
| o-Isobutylethylbenzene | — | trace | — | 0.1 |
| m-Isobutylethylbenzene | — | 1.6 | — | 3.0 |
| p-Isobutylethylbenzene | — | 1.0 | — | 1.9 |
| Triethylbenzene | — | — | — | — |
| Tetraethylbenzene | — | — | — | — |
| Pentaethylbenzene | — | — | — | — |
| Hexaethylbenzene | — | — | — | — |
| Others | — | 0.2 | — | 0.5 |
| Conversion of Isobutylbenzene (wt %) | 4.6 | | 9.3 | |

TABLE 11-continued

|  | Comparative Example 1 | Comparative Example 2 |
| --- | --- | --- |
| Selectivity of p-Isobutylethylbenzene (mol %) | 36.0 | 36.5 |
| Isobutylethylbenzene (o/m/p) | 0/62/38 | 2/60/38 |

Comparative Example 3

Following the same procedure as in Experimental Example 33, p-sec-butylethylbenzene (purity=97.5% by weight) was subjected to dehydrogenation reaction. The results are set forth in Table 12.

TABLE 12

| Reaction Temp. (°C.) | 550 |
| --- | --- |
| Contact Time (sec) | 0.20 |
| Molar Ratio of Steam | 93 |
| Conversion of PBE (%) | 43.4 |
| Composition of Reactants | |
| p-sec-butylethylbenzene | 55.4% by weight |
| p-sec-butylstyrene | 6.5% by weight |
| p-sec-butenylethylbenzene | 13.3% by weight |
| p-sec-butenylstyrene | 14.6% by weight |
| unidentified | 10.2% by weight |

The present invention has the following functional effects.

In the disproportionation step (I) of the present invention, a mixture containing three kinds of position isomers is produced by the disproportionation reaction of isobutylbenzene and a polyalkylbenzene represented by the formula (I) which is an ethylating agent, but it is apparent that p-isobutylethylbenzene can be separated and recovered from the three kinds of position isomers by distillation. Furthermore, with regard to the production ratio of the three kinds of position isomers in the mixture, isobutylethylbenzene of the o-isomer is characteristically formed in a much less amount as compared with the case where isobutylbenzene is reacted with ethylene in the presence of an acid catalyst. The boiling point of this o-isobutylethylbenzene is close to that of p-isobutylethylbenzene. Thus, of the three kinds of isomers of the mixture, o-isobutylethylbenzene is the component which is most difficult to separate from p-isobutylethylbenzene. Therefore, according to the reaction of the present invention which is characterized in that the production ratio of o-isobutylethylbenzene is low, the load of the distillation/purification operation of the reaction mixture can be alleviated remarkably, which is a large advantage.

Furthermore, a fraction other than p-isobutylethylbenzene fraction in the reaction product can be recycled as the raw material of the disproportionation step (I), with the result that the selectivity of p-isobutylethylbenzene of the isobutylbenzenes can be heightened.

In the ethylation by the disproportionation reaction using an acid catalyst, the selectivity of the p-isomer is relatively low, and for this reason, it is presumed that the above-mentioned technique can scarcely be employed as the reaction in which the p-isomer is the desired compound. In contrast, however, it is possible to get rid of the conventional limitation by the establishment of the above-mentioned technique, and even the ethylation by the disproportionation reaction using an acid catalyst is very economically advantageous.

When p-isobutylethylbenzene is subjected to dehydrogenation under conditions of the step (II) of the present invention, p-isobutylstyrene can be prepared in a high selectivity unexpectedly. Therefore, as described above, high-purity p-isobutylstyrene and unreacted p-isobutylethylbenzene can be obtained by subjecting the dehydrogenated reaction mixture obtained by the method of the present invention to two or three unit operations such as separation from an aqueous layer, drying and distillation. Moreover, needless to say, the unreacted p-isobutylethylbenzene can be recovered and then reused as the raw material for the dehydrogenation.

What is claimed is:

1. A method for preparing α-(4-isobutylphenyl)propionic acid or its precursor which comprises the following steps (I), (II), and (III):

step (I): subjecting isobutylbenzene and a polyalkylbenzene represented by the following formula (I) to disproportionation reaction at a reaction temperature of from $-10°$ to $600°$ C. in the presence of an acid catalyst in order to form p-isobutylethylbenzene

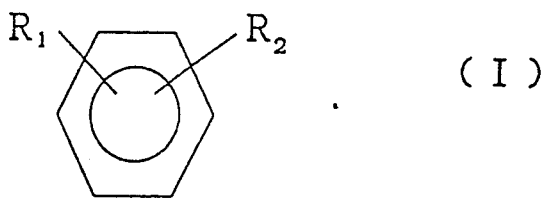

( I )

$R_1$ is $(-CH_3)_m$ or $(-C_2H_5)_m$, $R_2$ is $(-C_2H_5)_n$, and each of m and n is an integer of from 1 to 5 which meets $2 \leq m+n \leq 6$, step (II): dehydrogenating p-isobutylethylbenzene obtained in the above-mentioned step (I) at a reaction temperature of from $300°$ to $650°$ C. under a reaction pressure of 50 kg/cm² or less for a contact time of 0.005 to 20 seconds at a p-isobutylethylbenzene conversion of 80% by weight or less in a gaseous phase in the presence of a dehydrogenation metal catalyst containing a metal selected from the group consisting of metals in the groups Ib, IIb, VIa, VIIa and VIII of the periodic table in order to form p-isobutylstyrene, and step (III): the following step (IIIa) or (IIIb):

step (IIIa): reacting p-isobutylstyrene obtained in the preceding step (II) with carbon monoxide and hydrogen at a reaction temperature of from $40°$ to $150°$ C. under a mixed pressure of from 10 to 600 kg/cm² in the presence of a transition metal complex carbonylation catalyst in order to prepare α-(4-isobutylphenyl)propionaldehyde, or step (IIIb): reacting p-isobutylstyrene obtained in the preceding step (II) with carbon monoxide and water or a lower alcohol at a reaction temperature of from $40°$ to $250°$ C. under a carbon monoxide pressure of from 10 to 600 kg/cm² in the presence of a transition metal complex carbonylation catalyst in order to prepare α-(4-isobutylphenyl)propionic acid or its alkyl ester.

2. The method for preparing α-(4-isobutylphenyl)propionic acid or its precursor according to claim 1, wherein said acid catalyst is one selected from the group consisting of solid acid, inorganic acid, organic acid, Friedel-Crafts catalyst, heteropoly-acid and strong acid type ion exchange resin.

3. A method for preparing α-(4-isobutylphenyl)propionic acid or its precursor according to claim 2 wherein said acid catalyst in said step (I) is silica-alumina, and said reaction temperature is in the range of from $150°$ to $600°$ C.

4. A method for preparing α-(4-isobutylphenyl)propionic acid or its precursor according to claim 2 wherein said acid catalyst in said step (I) is trifluoromethanesulfonic acid, and said reaction temperature is in the range of from $-10°$ to $200°$ C.

5. A method for preparing α-(4-isobutylphenyl)propionic acid or its precursor according to claim 2 wherein said acid catalyst in said step (I) is hydrogen fluoride, and said reaction temperature is in the range of from $-10°$ to $200°$ C.

6. A method for preparing α-(4-isobutylphenyl)propionic acid or its precursor according to claim 2 wherein said acid catalyst in said step (I) is aluminum chloride, and said reaction temperature is in the range of from $0°$ to $150°$ C.

7. A method for preparing α-(4-isobutylphenyl)propionic acid or its precursor according to claim 2 wherein said acid catalyst in said step (I) is a heteropoly acid, and said reaction temperature is in the range of from $150°$ to $600°$ C.

8. A method for preparing α-(4-isobutylphenyl)propionic acid or its precursor according to claim 2 wherein said acid catalyst in said step (I) is a strong acid type cation exchange resin, and said reaction temperature is in the range of from $50°$ to $300°$ C.

9. A method for preparing α-(4-isobutylphenyl)propionic acid or its precursor according to claim 2 wherein said acid catalyst in said step (I) is an HX type zeolite, an HY type zeolite or hydrogen faujasite, and said reaction temperature is in the range of from $100°$ to $400°$ C.

10. A method for preparing α-(4-isobutylphenyl)propionic acid or its precursor according to claim 1 wherein said dehydrogenation metal catalyst in said step (II) is a catalyst containing a metal selected from the group consisting of iron, copper, zinc, nickel, palladium, platinum, cobalt, rhodium, iridium, ruthenium, chromium and molybdenum.

11. A method for preparing α-(4-isobutylphenyl)propionic acid or its precursor according to claim 1 wherein said metal of said dehydrogenation metal catalyst in said step (II) is at least one metal selected from the group consisting of iron, copper and chromium.

12. A method for preparing α-(4-isobutylphenyl)propionic acid or its precursor according to claim 1 which comprises oxidizing α-(4-isobutylphenyl)propionaldehyde obtained in said step (IIIa).

13. A method for preparing α-(4-isobutylphenyl)propionic acid or its precursor according to claim 1 which comprises hydrolyzing said alkyl α-(4-isobutylphenyl)propionate obtained in said step (IIIb).

* * * * *

UNITED STATES PATENT AND TRADEMARK OFFICE
CERTIFICATE OF CORRECTION

PATENT NO. : 5,166,419
DATED : November 24, 1992
INVENTOR(S) : Yuuichi Tokumoto, et al.

It is certified that error appears in the above-identified patent and that said Letters Patent is hereby corrected as shown below:

Column 1, line 13: "propiopic" should read as --propionic--

Column 6, lines 14-15: "preferably" should read as --preferably from -5 to 150°C.--

Column 10, line 35: "5-fold" should read as --15-fold--

Column 12, line 54: "20.hours." should read as --20 hours.--

Column 25, line 15; delete "reaction"

Column 26, line 55: "a-" should read as --$\alpha$- --

Column 27, line 39: "kg/cm$^2$" should read as --ch/cm$^2$.--

Column 27, line 61: "was the" should read as --was 0%, the--

UNITED STATES PATENT AND TRADEMARK OFFICE
CERTIFICATE OF CORRECTION

PATENT NO. : 5,166,419

DATED : November 24, 1992

INVENTOR(S) : Yuuichi Tokumoto, et al.

It is certified that error appears in the above-identified patent and that said Letters Patent is hereby corrected as shown below:

Column 32, line 58, Claim 12: delete "or its precursor--

Column 32, line 62, Claim 13: delete "or its precursor--

Signed and Sealed this

Twenty-first Day of December, 1993

Attest:

BRUCE LEHMAN

Attesting Officer      Commissioner of Patents and Trademarks